United States Patent
Vorm

(10) Patent No.: US 10,175,210 B2
(45) Date of Patent: *Jan. 8, 2019

(54) FLOW CONTROL IN HIGH PERFORMANCE LIQUID CHROMATOGRAPHY

(71) Applicant: PROXEON BIOSYSTEMS A/S, Odense C (DK)

(72) Inventor: Ole Vorm, Odense M (DK)

(73) Assignee: PROXEON BIOSYSTEMS A/S, Odense C (DK)

( * ) Notice: Subject to any disclaimer, the term of this patent is extended or adjusted under 35 U.S.C. 154(b) by 117 days.

This patent is subject to a terminal disclaimer.

(21) Appl. No.: 15/155,729

(22) Filed: May 16, 2016

(65) Prior Publication Data

US 2016/0258911 A1    Sep. 8, 2016

Related U.S. Application Data

(63) Continuation of application No. 12/865,789, filed as application No. PCT/EP2009/050697 on Jan. 22, 2009, now Pat. No. 9,370,729.

(60) Provisional application No. 61/026,507, filed on Feb. 6, 2008.

(51) Int. Cl.
| | |
|---|---|
| *G01N 30/32* | (2006.01) |
| *B01D 15/16* | (2006.01) |
| *G01N 30/36* | (2006.01) |

(52) U.S. Cl.
CPC ........... *G01N 30/32* (2013.01); *B01D 15/163* (2013.01); *G01N 30/36* (2013.01); *G01N 2030/324* (2013.01); *G01N 2030/326* (2013.01)

(58) Field of Classification Search
CPC .......... B01D 15/163; G01N 2030/324; G01N 2030/326; G01N 30/32; G01N 30/36
See application file for complete search history.

(56) References Cited

U.S. PATENT DOCUMENTS

| | | | | |
|---|---|---|---|---|
| 3,902,848 | A | * | 9/1975 | Juvet, Jr. ................ G01N 30/64 324/71.4 |
| 4,832,575 | A | | 5/1989 | Miller et al. |
| 5,236,847 | A | | 8/1993 | Satake et al. |
| 5,249,929 | A | * | 10/1993 | Miller, Jr. ............. F04B 11/005 222/146.5 |
| 5,457,626 | A | | 10/1995 | Wolze |
| 5,517,537 | A | * | 5/1996 | Greene ................... G01M 3/24 376/216 |
| 5,561,784 | A | * | 10/1996 | Chen ....................... G06F 8/433 711/157 |

(Continued)

FOREIGN PATENT DOCUMENTS

| | | |
|---|---|---|
| EP | 0 781 995 A | 7/1997 |
| JP | 05-256834 A | 10/1993 |
| WO | WO 2004/027535 A | 4/2004 |

*Primary Examiner* — John Fitzgerald
(74) *Attorney, Agent, or Firm* — Merchant & Gould P.C.

(57) ABSTRACT

A method for controlling the flow of liquid in a high performance liquid chromatography apparatus. The method includes operating a pump, measuring the liquid pressure downstream of the pump, measuring the liquid flow rate downstream of the pump, and controlling the operation of the pump. In the method, it is automatically determined whether the pump is controlled to achieve a desired pressure or controlled to achieve a desired flow rate. Fuzzy logic can be applied in the method to determine the switch between the control modes.

17 Claims, 1 Drawing Sheet

(56) References Cited

U.S. PATENT DOCUMENTS

| | | | |
|---|---|---|---|
| 5,564,550 A | 10/1996 | Van Rooy | |
| 5,600,211 A * | 2/1997 | Luger | H05B 41/36 |
| | | | 315/209 R |
| 5,748,467 A | 5/1998 | Qin | |
| 5,887,977 A * | 3/1999 | Morikawa | B01F 5/0604 |
| | | | 138/42 |
| 5,956,464 A | 9/1999 | Madni | |
| 6,488,858 B2 | 12/2002 | Tanimura | |
| 6,627,075 B1 | 9/2003 | Weissgerber et al. | |
| 6,718,164 B1 | 4/2004 | Korneluk | |
| 6,962,658 B2 | 11/2005 | Neyer et al. | |
| RE39,051 E | 3/2006 | Harnett | |
| 7,655,477 B1 | 2/2010 | Schneider | |
| 8,097,472 B2 * | 1/2012 | Schneider | G01N 33/558 |
| | | | 436/514 |
| 8,741,149 B2 * | 6/2014 | Hughes | G01N 30/10 |
| | | | 210/198.2 |
| 8,859,296 B2 * | 10/2014 | Schneider | G01N 33/558 |
| | | | 436/514 |
| 9,370,729 B2 * | 6/2016 | Vorm | B01D 15/163 |
| 2001/0030158 A1 | 10/2001 | Tanimura | |
| 2004/0232080 A1 | 11/2004 | Neyer et al. | |
| 2005/0109698 A1 | 5/2005 | Gerhardt et al. | |
| 2005/0236314 A1 | 10/2005 | Neyer et al. | |
| 2008/0015746 A1 | 1/2008 | Bertazzoni | |
| 2008/0121576 A1 * | 5/2008 | Gerhardt | G01F 1/363 |
| | | | 210/101 |
| 2010/0011842 A1 * | 1/2010 | Hoyle | G01N 33/557 |
| | | | 73/61.41 |
| 2010/0155243 A1 | 6/2010 | Schneider | |
| 2011/0204533 A1 * | 8/2011 | Winchester | A61K 9/5031 |
| | | | 264/4.6 |
| 2012/0080316 A1 * | 4/2012 | Schneider | G01N 33/558 |
| | | | 204/603 |
| 2015/0008130 A1 * | 1/2015 | Schneider | G01N 33/558 |
| | | | 204/603 |

* cited by examiner

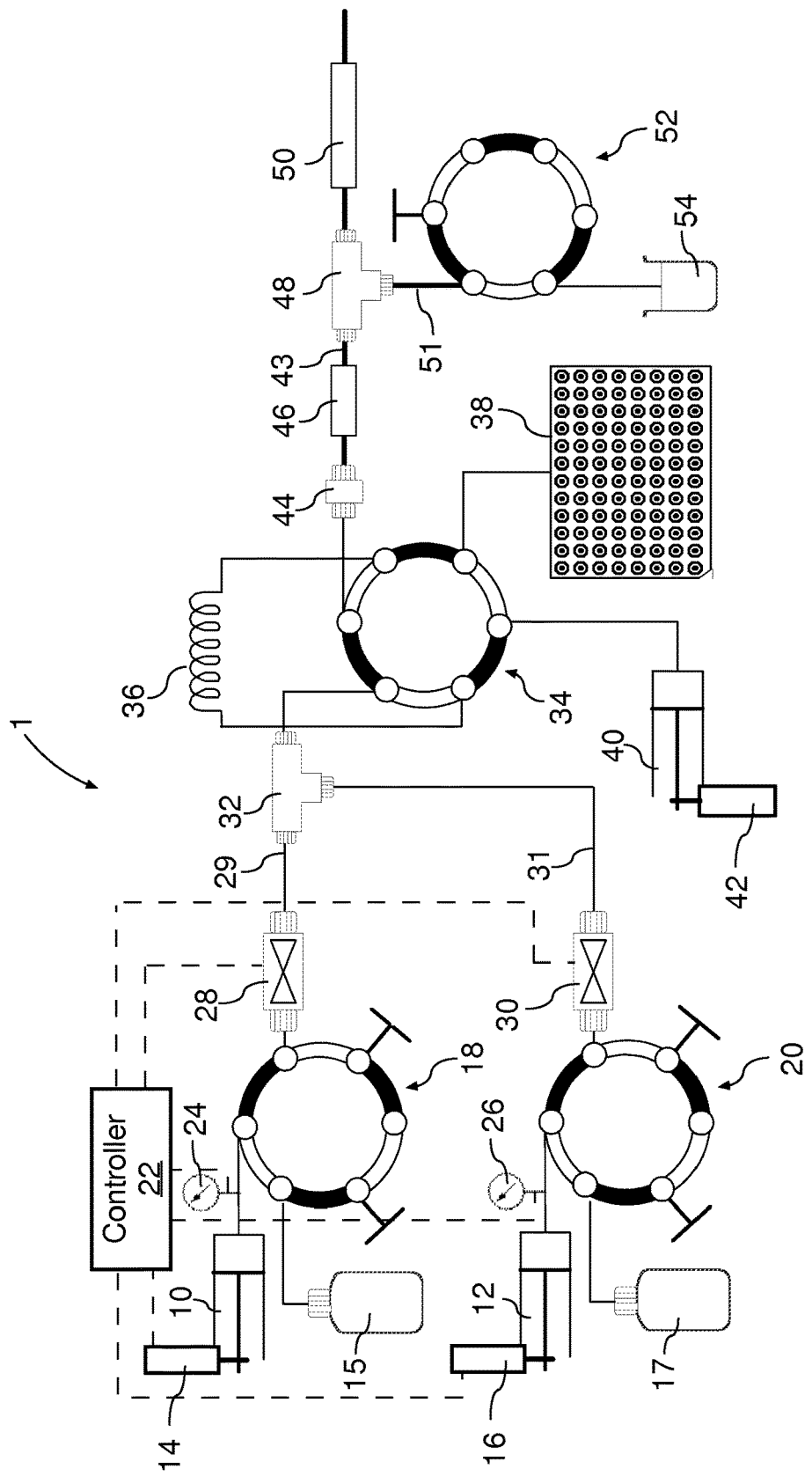

FLOW CONTROL IN HIGH PERFORMANCE LIQUID CHROMATOGRAPHY

This application is a Continuation Application of U.S. patent application Ser. No. 12/865,789, filed 28 Sep. 2010, now U.S. Pat. No. 9,370,729, which is a National Stage Application of International Patent Application No. PCT/EP2009/050697, filed 22 Jan. 2009, which claims benefit of Ser. No. 61/026,507, filed 6 Feb. 2008 in the United States and which applications are incorporated herein by reference. To the extent appropriate, a claim of priority is made to each of the above disclosed applications and a claim of priority is made to U.S. Pat. No. 9,370,729.

The present application relates to flow control in liquid chromatography and in to particular reverse phase HPLC (High Pressure (or Performance) Liquid Chromatography) devices and methods.

BACKGROUND OF THE INVENTION

HPLC is used ubiquitously for both analytical and preparative separation of molecules in diverse areas such as research, development and production in chemistry, pharmaceuticals, biotechnology, fundamental life science studies, etc.

One particular use of HPLC is in the field of proteomics, i.e. the study of the entire protein complement of a cell or tissue sample where proteolytic fragments of proteins (e.g. peptides) are separated by HPLC prior to detection by mass spectrometry. Since the samples being analyzed in proteomics experiments are typically very complex and available in only very low quantities, it is frequently a challenge to obtain sufficient sensitivity and analysis speed.

Sensitivity is obtained by using low flow rates for the mobile phase in combination with nano-bore columns (i.e. columns of narrow inner diameter). This approach however often leads to back pressures that are in excess of the instrumental system tolerances, which may cause system failure and also in many cases requires prolonged analysis times, which in turn leads to poor duty cycles for the overall LC-MS analysis. These back pressure and duty cycle problems affect many other application areas beyond proteomics as well.

In known proteomics, typical experimental HPLC conditions and parameters currently are:

Flow range: 100 nL/min-500 nL/min (also called nano-LC)

Pressure range: 50 atm.-600 atm.

Liquid phases are typically:

A-buffer: Mainly aqueous, often acidified and containing additives, with no or low organic content B-buffer: Mainly organic, often acidified and containing additives, with no or low water content Gradients are typically: From no or low percentage B-buffer to high percentage B-buffer in 5 to 600 minutes. Standard gradients could be from 5% B to 90% B in 30 minutes.

Stationary phases are typically:

Beads of various materials, often highly porous, diameters of 1.5 μm-5 μm, hydrophobic coating of hydrocarbons (C8 or C18) with chemical end-cap (non-hydrocarbon functional group)

Column sizes are typically:

ID: 25 μm to 250 μm

Length 1 cm to 200 cm

The operation of reverse phase nano-HPLC (or rather, the execution of an analysis cycle) can be separated into several chronologically distinct steps:

1. Loading of sample; either from an auto-sampler or by manual injection with a syringe into a sample loop. Sample volumes in nano-LC applications are typically 0.5 μL to 10 μL (but can be 10 times larger or smaller than this range).
2. Re-location of the loaded sample from the loop and onto the column.
3. De-salting of the immobilized sample by a volume of buffer (typically 100% A-buffer, i.e. with little or no organic solvent). This volume is typically 1.5 to 3 times larger than the volume from which the sample was loaded (e.g. a 5 μL sample injection would be de-salted with 7.5 μL to 15 μL of buffer) but the de-salting buffer volume can also be much larger or smaller than this range.
4. The elution and separation step. This is either done as isocratic elution (i.e. where the buffer composition remains constant during the elution step) or as a gradient where an continuously increasing ratio of organic is used.
5. A column cleaning step where all analytes of interest have been eluted but an extra high concentration of organic solvent is applied to the column in order to remove strong-binding molecules prior to the next analysis cycle. Such molecules would typically include pollutants such as organic polymers, surfactants, and very large bio-molecules that would interfere with subsequent separations if allowed to accumulate on the solid phase material.
6. A column re-equilibration step wherein the high-organic buffer inside the column is displaced with pure A-buffer such that the solid phase material can bind the next sample that is loaded.

Steps 5 and 6, or just step 6, can also be performed as the first step instead of being the last step(s) of the cycle. The above six steps of the operation can also be classified differently and be sub-divided into yet other steps.

The flow rates may change widely from step to step and also within each step. It is possible to regulate the flow and obtain working chromatography by regulating pump speeds such that the system strives to achieve a requested back pressure. This method of "pressure regulated flow control" is unfortunate inasmuch as it can lead to highly variable and badly controlled flow rates. Hence this control method is now very rarely used, and a more common way to regulate the pump speeds is by controlling for the actual absolute flow rates as measured by flow rate sensors somewhere downstream of the pump. Hereinafter, these two different modes of pump regulation will be referred to as "pressure control" and "flow control", respectively.

In the prior art the above steps, that encompass one analysis cycle, are either regulated by pressure control or flow control, with flow control being by far the most commonly used regulatory method. On some prior art systems, the pressure and flow during analysis execution are not regulated at all.

The detection efficiency by means of electrospray mass spectrometry is dependent on the analyte concentration at the time of ion formation, so the best sensitivity is achieved when analytes are eluted in volumes that are as small as possible.

This is done by using columns of narrow inner diameters and low flow rates. The narrow inner diameter of columns causes a large resistance to the flow of the mobile phase. Although the columns are filled with stationary phase material, the flow through the columns and the LC transfer lines is largely following Poiseulle's Law concerning the laminar flow of a Newtonian fluid in circular tubes. The Poiseulle equation states that the flow resistance is proportional to the length of the column and the viscosity of the mobile phase, while it is also inversely proportional to the column radius to its fourth potential. Hence, the resistance increases as columns become longer and narrower, especially during times of the analysis where the organic solvent ratio of the mobile phase is low. The "back-pressure" of the LC system is hereinafter considered as being the pressure delivered by the LC pumps in order to obtain a desired flow. Every LC system has an upper limit of its back-pressure above which either safety mechanisms will turn off the pumps (thereby halting the analysis) or system components will begin to fail (e.g. valves, seals, and fittings will break or leak).

In any case, it is currently necessary to take extraordinary care to ensure the back pressure does not exceed the system limitations at any point of the analysis cycle. For that reason, it is customary to perform a few "dry-runs" and monitor the back-pressure whenever a new column, or a new mobile phase, or a new method is deployed. Then the analysis parameters are typically adjusted such that the maximum back-pressure lies well below the system limits, including an extra safety margin since it is an established problem that columns exhibit increasing back-pressure contributions over time (owing to the accumulation of particulate debris at the column front and in-between column beads). The system's back-pressure limitation typically does not put any severe constraints on the execution of analyses during the part of the execution where the analytes are eluted (during the gradient), since that is typically done using very low flow rates (which in turn leads to a low back pressure).

However, in order to save considerable amounts of analysis time, it is typically advantageous to significantly increase the flow rates during the parts of the analysis cycle where: i) a sample is loaded onto a column; ii) the column or sample is being de-salted; and iii) the column is being re-equilibrated. During such parts of the analysis cycle, the system back pressure limitation poses severe constraints, and experimental parameters must (with current technology) be selected with a substantial safety margin, thereby leading to loss of analysis time. Otherwise, the execution will fail with substantial frequency, thereby leading to loss of samples and/or instrument damage and/or subsequent loss of time (since samples have to be re-analyzed).

Typical prior art nano liquid chromatography systems have upper back-pressure limits of around 5,000 PSI (340 bar), whereas some systems are designed to remain operational at over 10,000 PSI and are called Ultra-high performance liquid chromatography systems (UPLC). UPLCs are however designed to take advantage of columns that in general elevates the back pressure, so the general problem remains and one must still take active steps to avoid an "over-pressure" situation during all parts of the analysis cycle.

DISCLOSURE OF THE INVENTION

On this background, it is an object of the present application to provide a method for controlling fluid flow in a liquid chromatography apparatus that overcomes or at least reduces the drawbacks indicated above, i.e. a method that alleviates the problems of excessive back pressures and long duty cycles.

This object is achieved by providing a method for controlling fluid flow in a liquid chromatography apparatus, the method comprising driving said flow with a pump, controlling said fluid flow by either measuring the pressure of said liquid and in response thereto adjusting the output of said pump to achieve a target fluid pressure, or measuring the fluid flow of said liquid and in response thereto adjusting the output of said pump to achieve a target flow rate, and automatically switching or balancing between pressure based fluid flow control and flow rate based fluid flow control.

Thus according to the invention there is switching between the two modes of control or there can be a mix of the two control modes in an automatically determined balance. By automatically switching or balancing between the pressure control mode and the fluid flow rate control mode, the more optimal control mode for the actual circumstances can be used.

The target fluid pressure and/or the target flow rate can be variable during the execution of the method.

The method may further comprise involving fuzzy logic algorithms for deciding when to switch between said pressure based fluid flow control and flow rate based fluid control.

By applying fuzzy logic, it becomes possible to concurrently optimize the analysis speed, while greatly improving both the ease-of-use of the apparatus and the certainty of flawless analysis execution.

Fuzzy logic is a computationally straightforward and very robust way to obtain a working regulatory mechanism that works well both under standard conditions as well as under extreme conditions and during unfortunate events such as e.g. instant line blockage.

The liquid chromatography apparatus can be operated in an analysis cycle that involves a plurality of chronological steps that have different fluid flow requirements, and one or more of said steps being predetermined to be operated with either flow rate based control or pressure based control.

One or one or more of said steps may not be predetermined to be operated with a particular one of the flow rate based control or pressure based control mode, and the control mode in these steps is determined on the basis of measured parameters relating to operation of the liquid chromatography apparatus.

The fuzzy logic can have the current flow rate and the current pressure downstream of the pump as the input parameters.

The fuzzy logic output parameter can be the pump speed.

The fuzzy logic can be arranged and divided into a plurality of overlapping fuzzy sets. The fuzzy logic sets can be configured to give both course- and fine-grain regulation characteristics.

The output variable of the fuzzy logic can be arranged into a plurality of discrete singleton outputs, which are subsequently defuzzified into a control value by a center of gravity method.

The fuzzy variables can be featured in a plurality of rules, aiming to optimize flow, while at the same time ensuring that a maximum pressure is not exceeded.

Rules pertaining to pressure regulation can be prioritized by rule factors, so that pressure regulation will take precedence over any flow optimization, when the regulator operates in that section of the input space.

The fuzzy logic flow control may comprise an iterating loop that takes the sensor readouts, supplies them to a fuzzy logic engine and has the fuzzy logic engine re-evaluate its flow output.

The output difference maybe calculated relative to the previous output value and said difference is clamped into a specific range, added to the previous output value, and supplied to the pump as a new pump speed.

The object above can also be achieved by providing a liquid chromatography apparatus comprising at least one pump, a flow rate sensor downstream of said pump, a pressure sensor downstream of said pump, and a pump controller coupled to said pump, to said flow rate sensor and to said pressure sensor, said pump controller being configured to automatically switch between or balance pressure based pump control and flow rate based pump control.

Preferably, the pump controller includes a fuzzy logic engine.

Object above can also be achieved by providing a computer readable medium including at least computer program code for controlling the operation of a pump and program code for automatically switching between or balance a pressure control mode and a flow rate control mode.

Preferably, the computer readable medium includes program code for applying fuzzy logic.

Further objects, features, advantages and properties of the method, apparatus and computer readable medium according to the invention will become apparent from the detailed description.

BRIEF DESCRIPTION OF THE DRAWINGS

In the following detailed portion of the present description, the invention will be explained in more detail with reference to the exemplary embodiments shown in the drawings, in which:

FIG. 1 is a diagrammatic scheme of a liquid chromatography apparatus according to an embodiment of the invention.

DETAILED DESCRIPTION OF PREFERRED EMBODIMENTS

In the following detailed description, the apparatus, the method and the computer readable medium according to the teachings of this invention in the form of a liquid chromatography apparatus will be described by the embodiments.

FIG. 1 illustrates an embodiment of an apparatus according to an embodiment of the invention in the form of a high performance liquid chromatography apparatus.

The high performance liquid chromatography apparatus which is generally denoted with 1 is provided with a nano-liter syringe pump 10 that uses a direct drive crystal (sapphire) piston for delivering high pressure solvent A and a nano-liter syringe pump 12 that also uses a direct drive sapphire piston but in this case for delivering high pressure solvent B.

The syringe pump 10 is driven by stepper motor 14 to deliver pressure to solvent A (A-buffer) and the syringe pump 12 is driven by a stepper motor 16 to deliver pressure to solvent B (B-buffer). The outlet/inlet of the syringe pump 10 is connected to a first valve 18 and the outlet/inlet of the syringe pump 12 is connected to a second valve 20. Both first valve 18 and second valve 20 has two positions that are achieved by a 60° rotation. The little circles represent the six ports of the valve (not all ports are in use) and the thick black parts of the larger circle represent fluid connections whilst the white parts of the larger circle illustrate that there is no fluid connection between the ports concerned.

In the shown position first valve 18 connects the syringe pump 10 to conduit 29 that leads the fluid from the syringe pump towards the chromatography column 50. This position is e.g used during a sample run.

In the other of the two positions (not shown) the first valve 18 connects the syringe pump 10 to a canister 15 that contains solvent A. This position is used for refilling the syringe pump with solvent A.

In the shown position second valve 20 connects the syringe pump 12 to conduit 31 that leads the fluid from the syringe pump towards the chromatography column 50. This position is e.g. used during a sample run.

In the other of the two positions (not shown) the second valve 20 connects the syringe pump 12 to a canister 17 that contains solvent B. This position is used for refilling the syringe pump with solvent B.

A pressure sensor 24 measures the pressure in the liquid downstream of pump 10 and a pressure sensor 26 measures the pressure in the liquid downstream of pump 12. A flow sensor 28 in-line with conduit 29 measures the fluid flow rate of solvent A and a fluid flow sensor 30 measures the fluid flow rate of solvent B in conduit 31.

A controller 22 receives the sensor information from pressure sensor 24, pressure sensor 26, flow rate sensor and from flow rate sensor 30. The controller 22 is coupled to the stepper motor 14 and to the stepper motor 16 and issues a control signal to the stepper motor 14 and to the stepper motor 16. These control signals determine the speed of the stepper motors 14,16.

Conduit 29 and 31 (buffer lines) are joined at a narrow T piece/connector 32. The outlet of the T-connector 32 is coupled to a third (auto sampler) valve 34. The third valve 34 is similar to the first and second valves 18,20, in that it has six ports (all ports are in use) and two positions that are obtained by a 60° rotation. In the shown position in the third valve 34 connects the outlet of the T-piece to the conduit 43 that leads to column 50. In this position the third valve 34 also connects a sample plate (or microtiter plate) 38 with the samples to one end of a sample collecting coil 36 and connects the other end of sample collecting coil 36 to a syringe pump 40 that is driven by stepper motor 42.

This position of the third valve 34 is used to aspirate a sample from the sample plate 38 into the sample coil 36 by withdrawing the piston of the syringe pump 40 until the sample has moved into the sample coil 36. In the other of its two positions (not shown) the third valve 34 connects the outlet of the T-connector 32 to one end of the sample collecting coil 36 and the other end of the sample collecting coil 36 to conduit 43 that leads to the pre-column 46 and the column 50.

A connector 44 couples of the conduit 43 to the valve 34. Conduit 43 includes a pre-column 46, a T-connector 48 and the (main) column 50. One branch of the T-connector 48 is connected to a waste conduit 51 that includes a fourth valve 52, that has two positions and six ports (only two ports are in use) and opens and closes the connection of conduit 51 to a waste container 54 by a 60° rotation of the valve.

Components 46, 48, 51, 52, and 54 are omitted in another embodiment of the chromatographic device (not shown). In this alternative embodiment the sample is relocated from the sample coil 36 directly onto the column 50 instead of onto the pre-column 46.

For practical reasons (i.e. to avoid that the drawing will be cluttered with non-essential information) the connections between the controller 22 and the third valve 34, the fourth valve 54 and the stepper motor 42 have not been shown in FIG. 1. It is understood that the first, second, third and fourth valve 10, 12, 34, 52 are controlled by the controller 22 and operate automatically without the interference of an operator or user. The controller 22 is configured to execute the complete analysis cycle automatically, based on pre-programmed instructions and commands entered by an operator.

The operation of reverse phase nano-HPLC (or rather, the execution of an analysis cycle) is in this embodiment of the invention separated into several chronologically distinct steps:
1. Loading of sample; either from the sample plate 38 or by manual injection with a syringe into the sample loop 36. Sample volumes in nano-LC applications are typically 0.5 µL to 10 µL (but can be 10 times larger or smaller than this range).
2. Re-location of the loaded sample from the sample loop 36 and onto the pre-column 46 or the column 50 as the case may be.
3. De-salting of the immobilized sample by a volume of buffer (typically 100% A-buffer, i.e. with little or no organic solvent). This volume is typically 1.5 to 3 times larger than the volume from which the sample was loaded (e.g. a 5 µL sample injection would be de-salted with 7.5 µL to 15 µL of buffer.
4. The elution and separation step. This is either done as isocratic elution (i.e. where the buffer composition remains constant during the elution step) or as a gradient where an continuously increasing ratio of organic is used.
5. A column cleaning step where all analytes of interest have been eluted but an extra high concentration of organic solvent is applied to the column in order to remove strong-binding molecules prior to the next analysis cycle. Such molecules would typically include pollutants such as organic polymers, surfactants, and very large bio-molecules that would interfere with subsequent separations if allowed to accumulate on the solid phase material.
6. A column re-equilibration step wherein the high-organic buffer inside the column is displaced with pure A-buffer such that the solid phase material can bind the next sample that is loaded.

Steps 5 and 6, or simply step 6, can also be performed as the first step instead of being the last step of the cycle. These steps can also be classified differently and be sub-divided into yet other steps.

In prior art, the analysis method (i.e. the method according to which the analysis cycle is executed) is controlling the pump speed based on flow rate measurements from the two flow sensors during all six steps of the analysis cycle defined above.

According to the present embodiment of the invention, the conventional flow rate control algorithm in the controller 22 has been replaced in all steps except step 4 (the gradient, which is still strictly regulated for flow rate and A/B buffer ratio) and 5 (which is executed as an integral part of the gradient and hence uses the same control algorithms) by a control method that switches automatically between flow rate control and pressure control.

In an embodiment, the controller 22 has been provided with a fuzzy logic engine. In the fuzzy logic engine operates with mathematical logia technology, which operates with approximate reasoning based on logically defined sets.

Where classical bivalent predicate logic incorporates only discrete set relationships, resulting in either-or Bayesian inferences, fuzzy logic enables a more gradual view of set relations, with the ability to produce regulator inferences with diversified multi-objective responses. The behavior of an inference engine based on fuzzy sets—a fuzzy logic controller—is specified by fuzzy logic rules that share the syntax of conventional Bayesian logic, but they operate on input and output fuzzy sets, which semantically represent approximate reasoning and subsequent control. Input variables are converted into fuzzy set membership values, are handled by the fuzzy control rules, resulting in several piecewise output sets, which are finally "defuzzified" into a singular real output control value.

According to an embodiment a standard implementation of a fuzzy logic controller is described by the standardized (IEC 1131-7) Fuzzy Control Language (FCL), and in the present embodiment, with the following configuration:
Two input variables: the current flow and the current pressure, arranged and divided into 9-10 overlapping fuzzy sets, designed to give both course- and fine-grain regulation characteristics.
One output variable: the control flow given to the pump, arranged into 9 discrete singleton outputs, which are subsequently "defuzzified" into a control value by the "Center of Gravity" method (for singleton sets).

These fuzzy variables are featured in 12 rules, aiming to optimize flow, while at the same time ensuring a maximum pressure is not exceeded. Rules pertaining to pressure regulation are prioritized by rule factors, so that pressure (down-) regulation will take precedence over any flow optimization, when the regulator operates in that section of the input space. This allows for seamless multi-objective optimization.

In an embodiment of the specific implementation of the fuzzy logic control as used during the analysis cycle is as follows:

The fuzzy logic controller 22 is a specialized case of a conventional pump flow controller, which is a pluggable algorithm (known as a strategy) that alters the behavior of the pump 12, 14 depending on its implementation. For the pump (as a software device), the controller implementation is completely opaque, i.e. the pump is independent of how it works and is implemented. The controller has access to the readouts of the flow and pressure sensors downstream of the pump.

During the analysis cycle, different flow controllers (including the fuzzy logic controller) are plugged into the pump device, thereby taking control of how sensor feedbacks are interpreted and processed, and in turn, how pump flow is regulated. According to an embodiment of the invention, the specific controller used in each analysis step is preprogrammed.

In the analysis steps where fuzzy logic flow control is used (steps 2, 3 and 6), an iterating loop will take the sensor readouts (flow rate and pressure), supply them to the fuzzy logic engine and have it re-evaluate its flow output. The output difference is then calculated relative to the previous output value. This difference is clamped into a specific range, added to the previous output value, and supplied to the pump as a new flow rate (pump speed/speed of the stepper motor). Clamping is included to protect against fast changes in output flow rate, i.e. changes that are greater than the mechanical/electrical capabilities of the pump. The output flow rate is e.g. recalculated every 200 ms.

Steps 2, 3 and 6 are normally only restricted by system and/or column pressure limits, so for ease of use, the researcher (user/operator) is allowed to only specify a pressure limit and volume, but leave the flow rate parameter undefined. In this way the system can complete these steps at a flow rate as high as possible, i.e. as quickly as possible, without the researcher having to worry about a suitable flow rate to stay within pressure limits. On the other hand, if so desired, a flow rate can be specified by the operator, and the controller 22 will then try to deliver this particular flow, but still ensure the back pressure stays within the specified limits.

The fuzzy engine in the controller 22 uses rules featuring course and drastic changes when operating far from the typical flow setpoint value. When it operates near the setpoint, however, more fine-grained and detailed rules take over to ensure regulated control close to specifications. To enable the use of one fuzzy controller instance over the entire dynamic range of flow operating setpoints, the combined controller input and output sets are scaled when flow specifications differ from the original calibrated setting.

Thus, in an embodiment the controller 22 is configured to automatically switch between pressure control and flow rate control during one or more of the steps of the analysis cycle. In the pressure control mode the controller 22 regulates the speed of the respective syringe pump 10,12 by controlling the respective stepper motor 14,16 with the aim to maintain a desired pressure downstream of the pump concerned. The desired pressure may vary from step to step or during a step of the cycle. In the flow rate control mode the controller 22 regulates the speed of the respective syringe pump 10,12 by controlling the respective stepper motor 14,16 with the aim to maintain a desired flow rate downstream of the pump. The desired flow rate may vary from step to step or during a step of the cycle.

In another embodiment, the controller is configured to automatically switch between the pressure and flow control rate in one or more steps of the cycle on the basis of fuzzy logic.

During the elution and separation step in the flow rates of the pumps 10,12 needs to follow in exactly predefined profile, and automatic changing between pressure and flow control would not be useful in this step. However in the other steps of the cycle, significantly higher flow rates can be achieved by applying automatic switching between pressure control and flowrate control. Increased flow rates can be achieved in the steps where the automatic change between the control modes is applied and thereby the overall analysis cycle time can be reduced. An increasing advantage of such optimized switching between pressure control and flowrate control is obtained with decreasing cross-sectional area of the various columns and conduits in the high-performance liquid chromatography device 1. However, for steps in which the fluid does not need to be urged to the column 50, an increase in diameter of the conduits of the device will allow even further increased flow rates that also will be able to be exploited by a fuzzy logic-based controller and result in even further reduce its overall cycle times.

The various aspects of what is described above can be used alone or in various combinations. The teaching of this application is preferably implemented by a combination of hardware and software, but can also be implemented in hardware or software. The teaching of this application can also be embodied as computer readable code on a computer readable medium, i.e. a computer readable medium including at least computer program code for controlling the operation of a pump and program code for automatically switching between a pressure control mode and a flow rate control mode. In an embodiment the computer readable medium includes program code for applying fuzzy logic.

It should be noted that the teaching of this application is not limited to the use of a single controller or to a device with the exact configuration as described above.

The teaching of this application has numerous advantages. Different embodiments or implementations may yield one or more of the following advantages. It should be noted that this is not an exhaustive list and there may be other advantages which are not described herein. One advantage of the teaching of this application is that it provides for a method of controlling a pump of a liquid chromatography apparatus and for a liquid chromatography apparatus with an optimized analysis speed. Another advantage of the teaching of this application is that it provides for a method of controlling a pump of a liquid chromatography apparatus and a chromatography apparatus with an improved ease of use. Yet another advantage of the teaching of this application is that it provides for a method for controlling the pump of a chromatography apparatus and a chromatography apparatus with improved likelihood of flawless analysis execution.

Although the teaching of this application as been described in detail for purpose of illustration, it is understood that such detail is solely for that purpose, and variations can be made therein by those skilled in the art without departing from the scope of the teaching of this application.

For example, although the teaching of this application has been described in terms of a high-performance liquid chromatography apparatus with a syringe pump, it should be appreciated that the invention may also be applied to other types of pumps, such as piston pumps, reciprocating pumps, pneumatic pumps, hydraulic pumps, piezo-driven pumps, electrokinetic pumps, peristaltic pumps and the like. It should also be noted that there are many alternative ways of implementing the methods and apparatuses of the teaching of this application. For example, although the pump controller has been described in terms of a dedicated control unit, it should be noted that other controllers can be used. For example, a general-purpose computer or the like may be used in some configurations of the liquid chromatography apparatus.

The term "comprising" as used in the claims does not exclude other elements or steps. The term "a" or "an" as used in the claims does not exclude a plurality. The single processor or other unit may fulfill the functions of several means recited in the claims.

The invention claimed is:

1. A method for controlling fluid flow in a liquid chromatography apparatus, said method comprising:
    driving said fluid flow with a pump;
    controlling said fluid flow by:
        (i) a pressure based fluid flow control comprising measuring the pressure of said liquid and in response thereto adjusting the output of said pump to achieve a target fluid pressure; and
        (ii) a flow rate based fluid flow control comprising measuring the fluid flow of said liquid and in response thereto adjusting the output of said pump to achieve a target flow rate; and
    automatically switching or balancing between said pressure based fluid flow control and said flow rate based fluid flow control;
    said method further comprising applying fuzzy logic algorithms for deciding when to switch or how to balance between said pressure based fluid flow control and flow rate based fluid control; and
    wherein said target fluid pressure and/or said target flow rate are variable during execution of the method.

2. A method according to claim 1, wherein the fuzzy logic algorithms have current flow rate and current pressure downstream of the pump as input parameters.

3. A method according to claim 1, wherein the fuzzy logic output parameter is the pump speed.

4. A method according to claim 1, wherein output variable of the fuzzy logic algorithms are arranged into a plurality of discrete singleton outputs, which are subsequently defuzzified into a control value by a center of gravity method.

5. A method according to claim 1, wherein the fuzzy logic algorithms comprises an iterating loop that takes sensor readouts, supplies them to a fuzzy logic engine and has the fuzzy logic engine re-evaluate flow output.

6. A method according to claim 1, wherein an output difference is calculated relative to a previous output value and said output difference is clamped into a specific range, added to the previous output value, and supplied to the pump as a new pump speed.

7. A method according to claim 1, wherein said method comprises automatically switching between said pressure based fluid flow control and said flow rate based fluid flow control.

8. A method according to claim 1, wherein said fuzzy logic algorithms are arranged and divided into a plurality of overlapping fuzzy sets.

9. A method according to claim 8, wherein said fuzzy sets are configured to give both course- and fine-grain regulation characteristics.

10. A method according to claim 1, wherein fuzzy variables are featured in a plurality of rules, aiming to optimize flow, while at the same time ensuring that a maximum pressure is not exceeded.

11. A method according to claim 10, wherein rules pertaining to pressure regulation are prioritized by rule factors, so that pressure regulation will take precedence over any flow optimization.

12. A method according to claim 1, wherein said liquid chromatography apparatus is operated in an analysis cycle that involves a plurality of chronological steps that have different fluid flow requirements, and one or more of said steps being predetermined to be operated with said flow rate based control and said pressure based control.

13. A method according to claim 12, wherein one or more of said steps are not predetermined to be operated with a particular one of said flow rate based control or said pressure based control, and the one or more steps are determined on the basis of measured parameters relating to operation of the liquid chromatography apparatus.

14. A method according to claim 12, wherein output is a function of time point relative to the overall analysis cycle of the apparatus.

15. A method according to claim 14, wherein output is different between the steps and can be modified with progression within each step.

16. A liquid chromatography apparatus comprising:
at least one pump;
a flow rate sensor downstream of said pump;
a pressure sensor downstream of said pump; and
a pump controller coupled to said pump, to said flow rate sensor and to said pressure sensor;
said pump controller is configured to automatically switch between or balance a pressure based pump control and a flow rate based pump control;
said pump controller includes a fuzzy logic engine for controlling the switch between or balance said pressure based pump control and said flow rate based pump control;
wherein said pump controller is configured to adjust output to achieve a target fluid pressure or a target flow rate; and
wherein said target fluid pressure and/or said target flow rate are variable.

17. A liquid chromatography apparatus according to claim 16, wherein said pump controller is configured to automatically switch between said pressure based pump control and said flow rate based pump control.

* * * * *